United States Patent [19]
Rishpon et al.

[11] Patent Number: 5,149,629
[45] Date of Patent: Sep. 22, 1992

[54] COULOMETRIC ASSAY SYSTEM

[75] Inventors: Judith Rishpon, Wolfson; Ilara Rosen, Ramat-Gan, both of Israel

[73] Assignee: Ramot University Authority for Applied Research and Industrial Development Ltd., Tel Aviv, Israel

[21] Appl. No.: 177,463

[22] Filed: Apr. 4, 1988

[30] Foreign Application Priority Data

Apr. 7, 1987 [IL] Israel .................................... 82131

[51] Int. Cl.$^5$ .................. G01N 33/53; G01N 33/552; C12M 1/40
[52] U.S. Cl. ..................................... 435/7.9; 435/7.5; 435/288; 435/291; 435/817; 436/527; 436/806
[58] Field of Search ............... 204/1 T, 403; 436/525, 436/527, 806; 435/7, 18, 21, 25, 26, 288, 291, 817, 7.9, 7.5

[56] References Cited

U.S. PATENT DOCUMENTS

| | | | |
|---|---|---|---|
| 4,228,237 | 10/1980 | Hevey et al. | 435/7 |
| 4,619,754 | 10/1986 | Niki et al. | 204/403 |
| 4,711,245 | 12/1987 | Higgins et al. | 204/403 |
| 4,713,165 | 12/1987 | Cononer et al. | 204/403 |

FOREIGN PATENT DOCUMENTS

0170375 2/1986 European Pat. Off. .

OTHER PUBLICATIONS

Robinson, G. A., et al., Biological Abstracts, vol. 82, Abstract No. 91756 (1986).
Strohl, A. N., et al., Chemical Abstracts, vol. 91, No. 1, Abstract No. 2042t (1979).

*Primary Examiner*—Esther L. Kepplinger
*Assistant Examiner*—Toni R. Scheiner
*Attorney, Agent, or Firm*—Browdy and Neimark

[57] ABSTRACT

The invention relates to a novel assay for the determination of entities having biological activity and to a device for carrying out such determinations. The assay is a very sensitive one and quantities in the picogram per milliliter range can be determined. The assay is based on chrono-coulometric measurements with sequential measurements of a plurality of samples being carried out with the aid of a multiplexer, in combination with a potentiostat, there being provided suitable electrodes and means for applying a predetermined voltage. One of the electrodes is advantageously a glassy carbon electrode, carbon felt or cloth or carbon paper. Amongst biologically active entities there are antibodies/antigens; hormones/receptors; nuclotides/nucleotide probes, one of the members of such a pair being immobilized on an electrode surface, being tagged with an enzyme providing a signal in coulometric measurements.

11 Claims, 8 Drawing Sheets

COULOMETRIC ASSAY SYSTEM

FIELD OF THE INVENTION

The invention relates to a novel assay for the determination of biomolecules by electrochemical means. The invention relates to such quantitative determinations based on the coupling of certain types of biomolecules to be determined to enzymes and to the use of electrochemical enzyme sensors bearing such enzymes. The invention further relates to a device for the rapid sequential determination of large numbers of samples, which is of considerable utility in large-scale determinations such as in clinics or hospitals.

BACKGROUND OF THE INVENTION

A wide variety of tests is used for the detection and for the quantitation of biomolecules. A high sensitivity is required for many of these as they are present in biological fluids in very small concentration. Furthermore, the assays must have a high degree of selectivity in order to be able to determine a specific biomolecule in the presence of other entities.

Many tests are based on the coupling of the species to be determined to another moiety and the subsequent determination of the labeled entity. There exist various assays based on the interaction of enzymes and their substrates; on the interaction of antigens and antibodies, between hormones and receptors, etc. There exists a wide variety of assays which are based on radioactive labels and on other types of labels.

The translation of selective interaction into a measurable quantity often implies coupling of a detectable labeling to one or more of the interacting species. Radioisotope labeling is one kind of such labeling which is used in analytical clinical laboratory.

However, the desire to avoid the use of radioactive techniques has stimulated the development of other labels. Among these enzymes appear to be practical: an enzyme is coupled with the bioactive material as a marker and the enzyme activity is measured. Enzyme labels increase the sensitivity through chemical amplification. Chemical amplification refers to the passing of a substance through a catalytic cycling, or multiplication mechanism to generate a relatively large amount of product. The rate at which the product is formed is related to the concentration of the analyte in the sample. The enzyme activity is usually measured by optical instruments such as colorimeters or spectrophotometers. The development of electrochemical bioassays has receive only little attention. Electrochemical methods are free of sample turbidity quenching, and interferences from the many absorbing and fluorescing compounds in typical biological samples that hinder spectroscopic techniques. Enzyme electrodes are an example of the combination of enzyme action with electrochemical measurements for analytical purposes. Enzyme electrodes are a type of biosensors. Biosensors are analytical devices in which biological materials capable of specific chemical recognition, are in intimate contact with transducers. Among these, bioelectrochemical sensors such as enzyme electrodes have found promising application especially in clinical and process measurements. Commercial analyzers equipped with enzyme sensors are available mostly for serum components measurements. There have been several attempts to construct other biosensors such as e.g. immunosensors.

However, at present amongst the disadvantages of such sensors are the following: The sensitivity is low as compared with established methods such as enzyme immuno-assays and a measuring cell is occupied for the whole incubation time to form an antigen-antibody complex. Therefore the advantages of electrochemical sensors-their short response time-is not exploited efficiently. Only a few samples can be measured per day and fast measurements are impossible. This is true especially in clinical tests which usually involve a large number of samples. The use of a single electrode and the calibration it requires prior to measurements impedes the measurements and does not allow its successful application in clinical tests in hospitals and clinics.

The system can be used to carry out assays with a wide variety of biointeractions. The invention is illustrated in the following with reference to a number of specific examples, which are to be construed in a non-limitative manner.

One of the representative enzymes which provide for a wide scope of substrates is alkaline phosphatase.

The enzyme alkaline phosphatase enzyme is a common label in immunological tests. Conjugates of antigens and antibodies with this enzyme are commercially available in a rather purified form. The common substrates for alkaline phosphatase used in various immunological tests are nitrophenyl phosphate and phenylphosphate. Electrochemical determinations of alkaline phosphatase based on the hydrolysis products of the enzyme reaction are rather difficult because of the high overvoltage of the phenol compounds and serious problems arising from adsorption to the electrode and fouling of the electrode response.

SUMMARY OF THE INVENTION

According to the present invention there is provided a convenient and rapid assay for the quantitative determination of a wide variety of molecules having a biological activity.

The invention further provides a device for the rapid and convenient chronocoulometric determination of such entities. There is provided an automated multi-sample and multi-electrode system for carrying out such determinations. There is further provided a convenient method of tagging of molecules to be determined, wherein alkaline phosphatase is used in conjunction with p-aminophenyl phosphate. Amongst entities which can be thus determined with a high degree of accuracy and very high sensitivity there may be mentioned antigens, antibodies, hormones, etc.

The multi-electrode system of the invention makes possible a rapid assay of a plurality of samples and is of special use in applications such as clinical and hospital use where a plurality of samples has to be analysed within as short a period of time as possible. The device comprises a plurality of enzyme electrodes, a counter-electrode and a reference electrode, there being provided means for rapidly switching over from one such electrode to another there further being provided a computerized system for the rapid recordal and evaluation of the results.

The basis of the measurement is based on the application of a predetermined voltage between the reference and the working electrode (say of the order of 0.zV for a certain enzyme); and measuring the electrical current at such voltage for each of the electrodes.

There are preferably provided means for the rotation of the electrodes as the measurement is being carried out. Each of the electrodes is first inserted into a different sample and incubated therein, and after this there is carried out the measurement in the device wherein there is provided a multiplexer, such sequential measurement in the same vessel being possible as the concentration of the solution does not undergo any appreciable change during such measurement. It is clear that the system illustrated herein, with 8 enzyme electrodes, is by way of example only and that there can be provided a larger number of such electrodes with suitable multiplexing and auxiliary equipment. For example, if an enzyme is to be determined which is an antigen, there can be bonded to a suitable electrically conducting electrode antibodies specific for such enzyme; the electrode is contacted with the sample containing the antigen, and if this is an enzyme which provides a product of reaction which reacts at the electrode, the electrode is introduced into an excess of substrate and the current is measured at a constant voltage, being indicative of the quantity of antigen. The measurement is always carried out when there is no saturation respective the antibodies. t is possible to use competitive methods of measurement where a given concentration of the tagged entity makes possible the determination of the untagged one by the determination of the ratio of these, measurements being made with various concentrations of the tagged moiety. The attachment of the desired entities (in this case antibodies) can be effected by chemical bonding or by mere adsorption. Details of the techniques used are set out in the experimental part. Experiments were carried out with IgG (anti-mouse IgG) which is a representative sample of any antigen and with dog IgG which is representative of an antigen-antibody system. Amongst hormones there may be mentioned the determination of aldosterone; HCG etc. which are representative of a wide variety of hormones. There may be attached to the electrode polyclonal or monoclonal antibodies, such as anti-IgG. It is possible to produce antibodies specific against certain hormones and to attach such antibodies to the electrode: for example insulin, $T_3$, $T_4$, etc., where the antibody has the function to serve as carrier making possible the reaction at the electrode set out above. The invention is illustrated with reference to the enclosed FIGS. in which:

Figure 1:
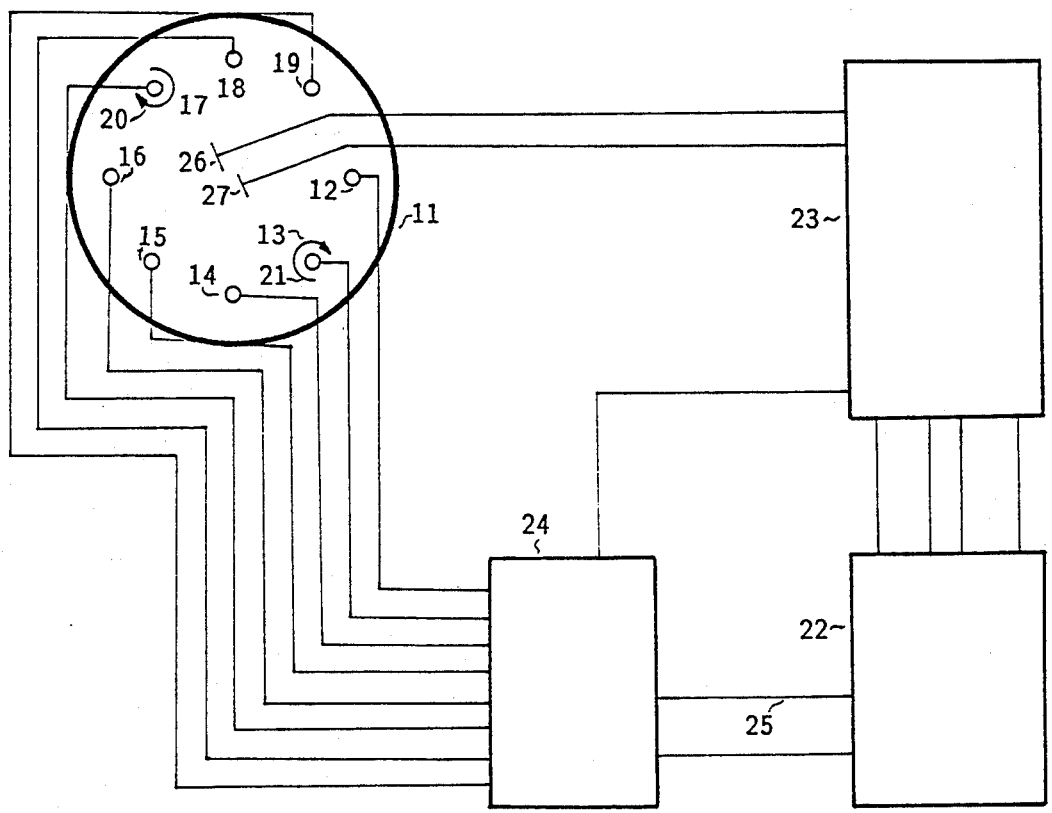
FIG. 1 is a schematic block diagram of a device of the invention.

The device of the invention is schematically illustrated herein with reference to FIG. 1.

Figure 2:
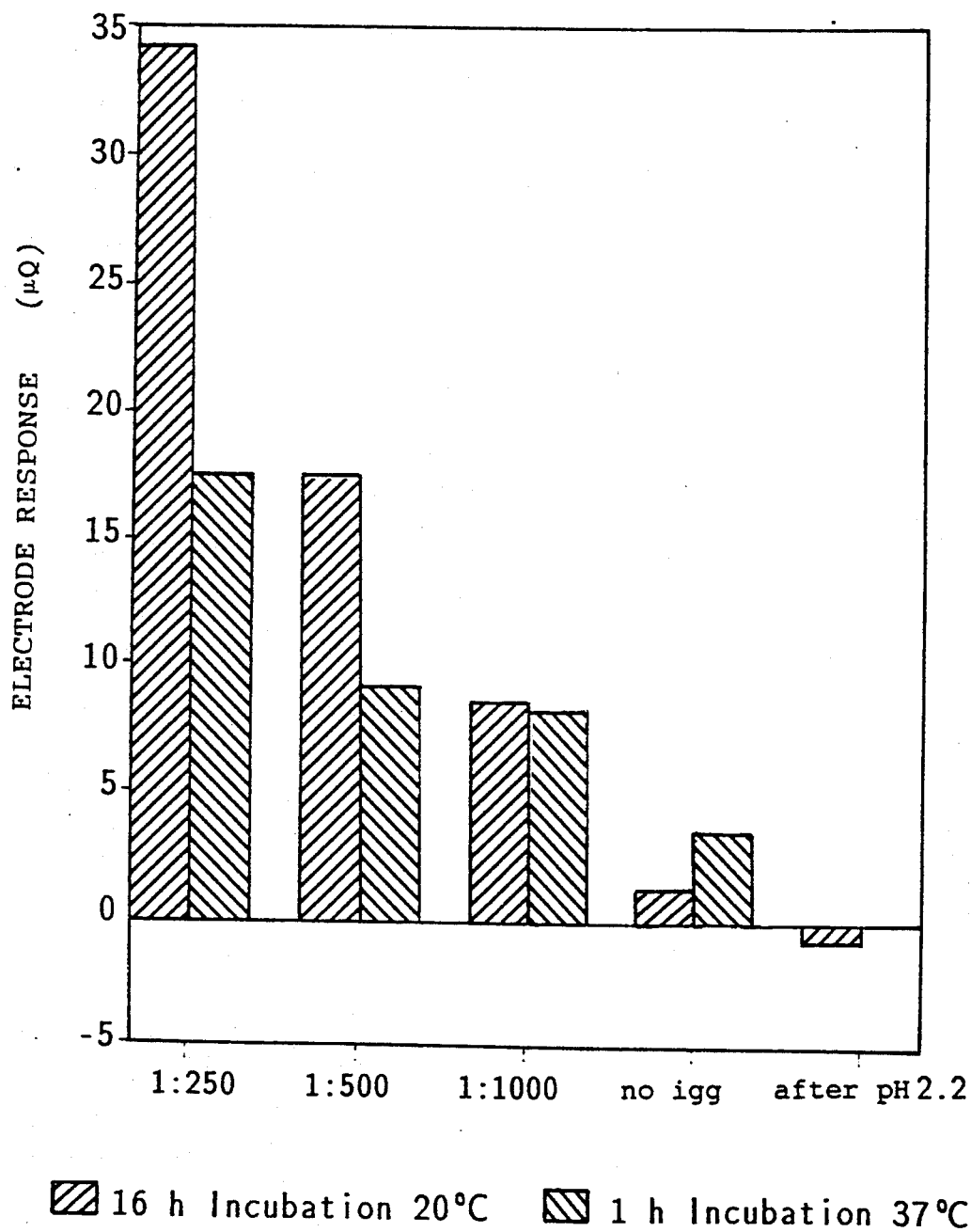
FIG. 2 illustrates the response of an mIgG electrode to the addition of amino-phenyl phosphate, with IgG concentrations indicated on the abscisa.

FIG. 2 illustrates the use of such system with an antimouse-IgG electrode, showing the effect of the addition of amino phenyl phosphate and the response of an mIgG electrode to such addition, with IgG concentration noted on the abscissa.

Figure 3:
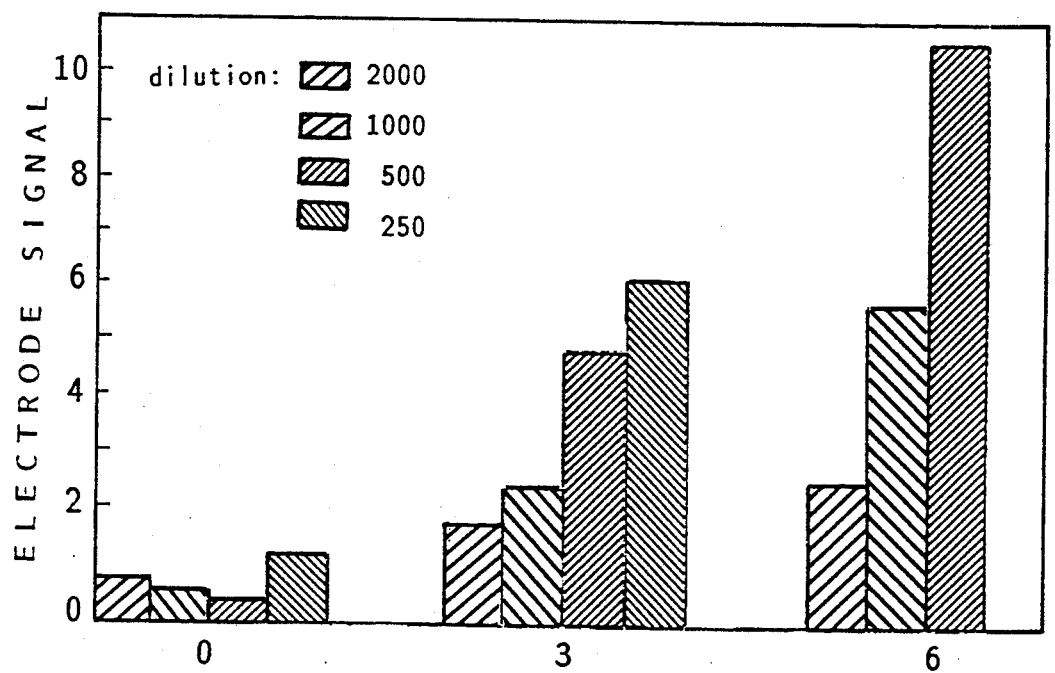
FIG. 3 illustrates the measurement of Dog IgG on an electrode of the invention, the measurement being with dog serum on the electrode.

FIG. 3 illustrates the determination of dog IgG: Different dog serums (diluted 1:10 in phosphate buffer pH 7.5 0.2M) were dried in the presence of carbodiimide on gold electrodes. The electrodes were then allowed to react with antidog IgG conjugate to alkaline phosphatase. The electrode signal was proportional to the IgG level in the dog serum that was on the electrode. The results are summarized in FIG. 3. The bars represent the electrode response to phenyl phosphate after incubation with different concentrations of antidog IgG alkaline phosphatase conjugates. The immunoglobulin concentration in the serum:

| Left bar | blank, no serum |
|---|---|
| Middle bars | serum IgG level 3 mg/ml |
| Right bars | serum IgG level 6 mg/ml. |

Measurements were done in the presence of 10 mM $MgCl_2$ and the solution was stirred by magnetic stirrer.

Figure 4:
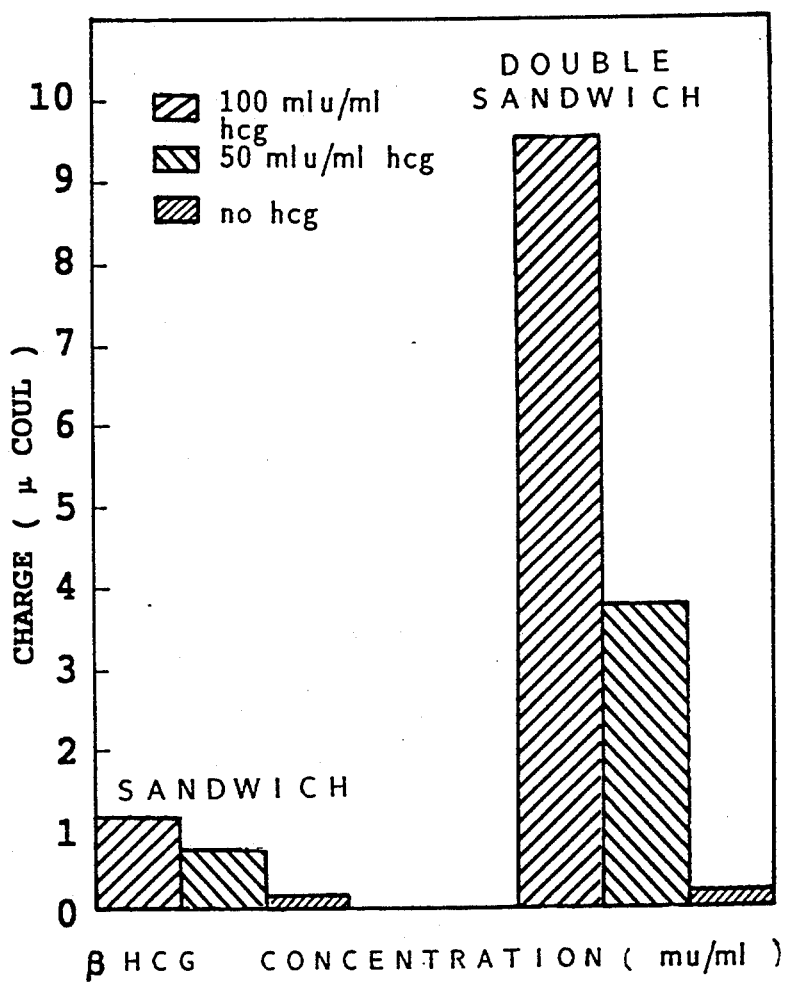
FIG. 4 illustrates the detection of $\beta$-HCG in urine.

In FIG. 4: illustrates the detection of $\beta$- HCG in urine.

Left bars—response of gc/aHCG (polyclonal) electrode to aminophenyl phosphate (2 mM) after incubation with urine samples containing different concentrations of HCG (1 hr, 37° C.) followed by ap-aHCG (monoclonal) (1 hr, 37° C.) (sandwich).

Right bars—Response of gc/a$\beta$-HCG (monoclonal) electrode to aminophenyl phosphate (2 mM) after incubation with urine samples followed by a$\beta$HCG (rb) (policlonal) and ap-arb IgG (1 hr, 37° C.) (double sandwich).

Figure 5:
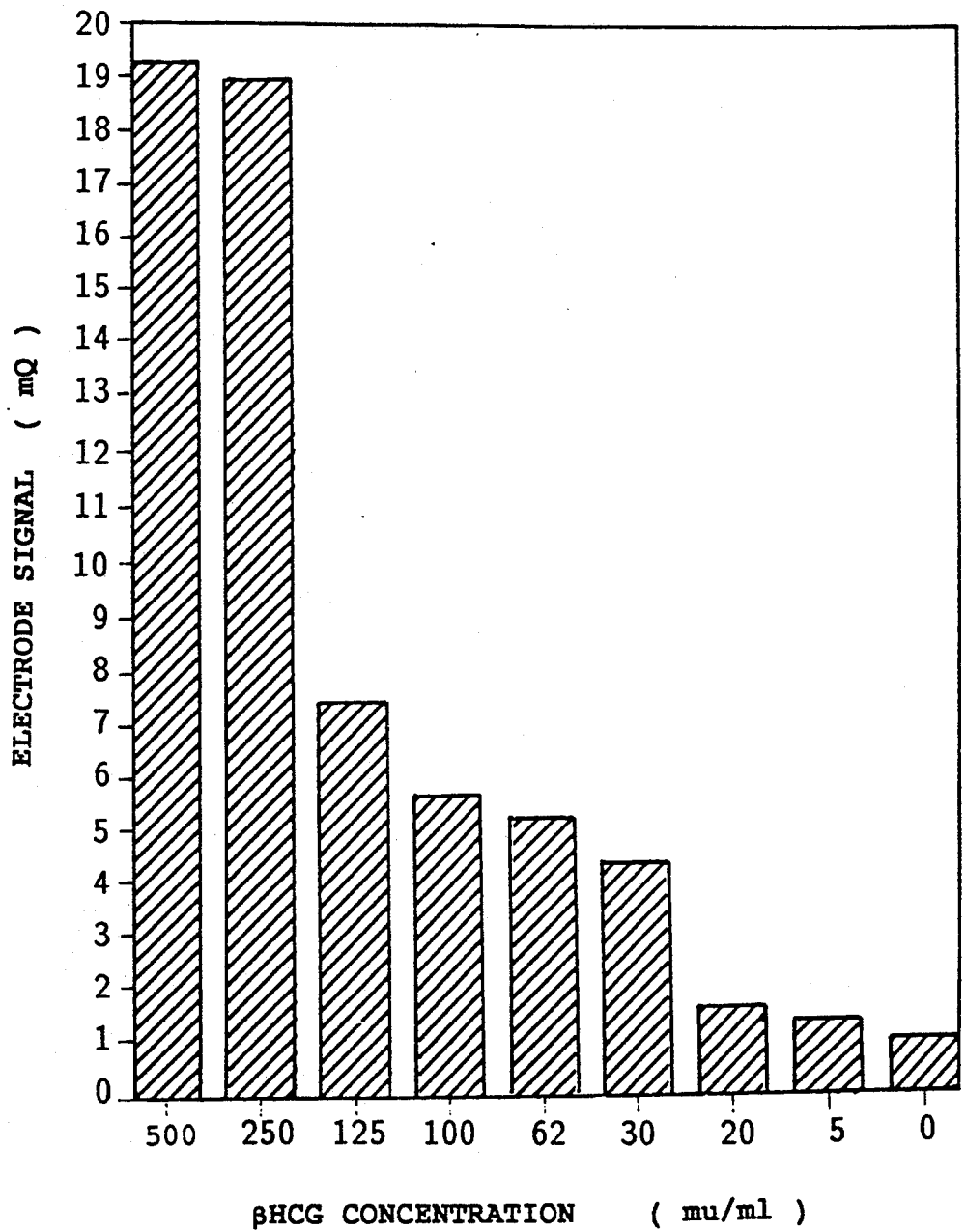
FIG. 5, illustrates the electrode response as a function of HCG concentration.
Figure 6:
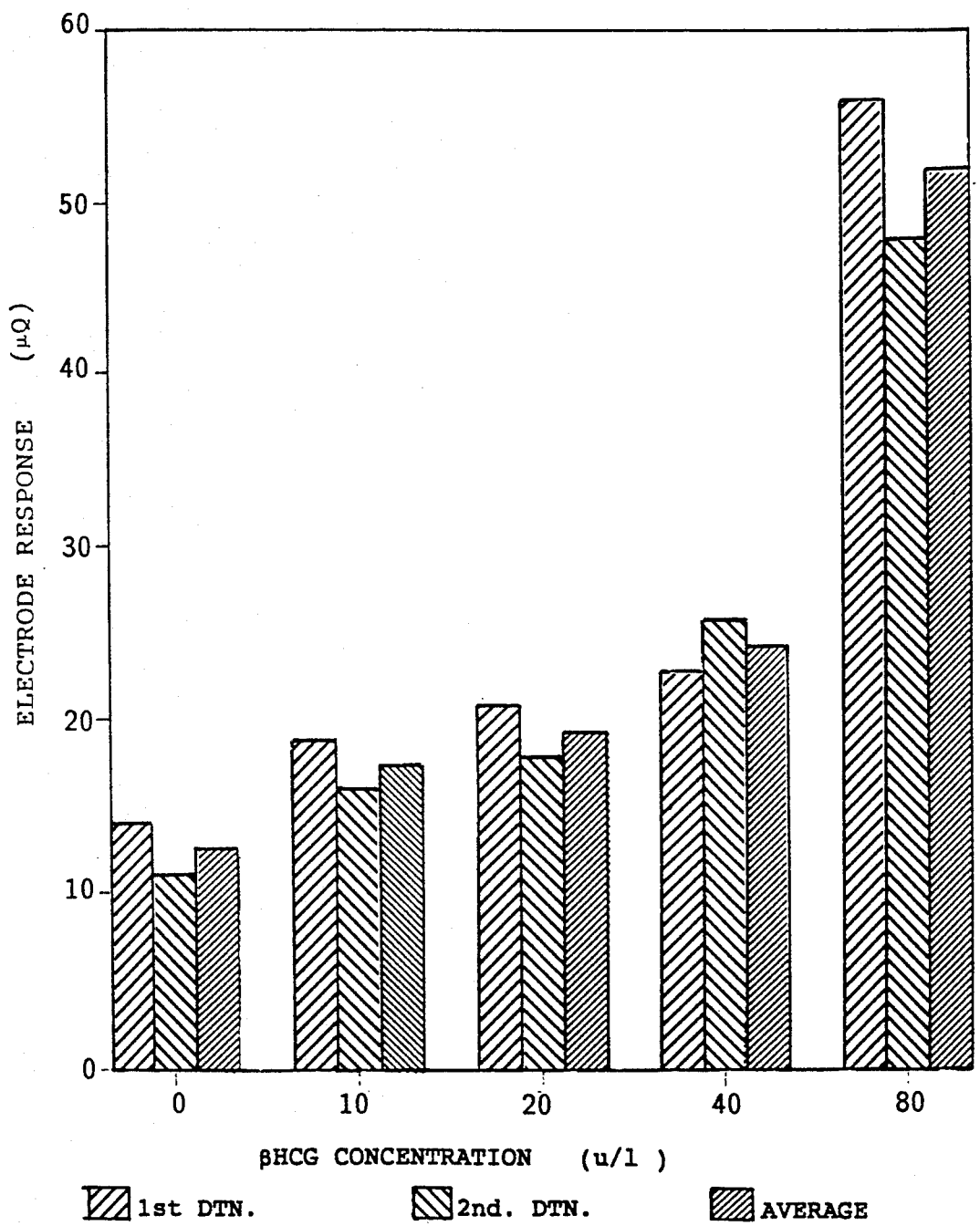
FIG. 6 illustrates the determination of $\beta$-HCG using carbon felts as support (electrode)

FIG. 5 illustrates the determination of $\beta$-HCG in serum. Electrode response as a function of $\beta$HCG concentration: Serum samples in which the HCG concentration was determined by radio immunoassay were diluted in PBS and incubated with electrodes on which monoclonal antiHCG was immobilized. The device for carrying out the assay with a plurality of samples in rapid sequence is illustrated with reference to FIG. 1, where this is illustrated in a schematical manner. The device comprises a vessel 11, shown in a view from above, wherein there are positioned a number of identical electrodes 12, 13 and 14, 15, 16, 17, 18 and 19, each of which is made of an electrically conducting inert material (such as carbon, graphite, gold-plated or platinum plated metal), in a rod shape, embedded in a non-conducting inert material such as teflon. Advantageously, each of the electrodes 12 to 19 is provided for means of axial rotation, as indicated by the arrows 20 and 21. Such rotation substantially decreases the period of time required for the biological interactions and thus decreases the time of measurement. The rotation also increases the electrode signal.

The system comprises a microcomputer 22, connected with a potentiostat 23, the connection being via a digital to analog port. The electrode assembly is connected to the potentiostat 23 and also via the multiplexer 24 to a parallel port 25 of the microcomputer 22. The electrodes 12 to 19 are all in the vessel 11 which contains the reference electrode 26 and the counterelectrode 27, which are also connected to the potentiostat 23. The mode of operation is amperometric, i.e. a potential is applied to the working electrode and the resulting current is measured. Each of the electrodes can be connected and disconnected at will, and thus by hopping from electrode to electrode, a plurality of measurements can be effected within a brief period of time. While such measurements are effected, the electrode in operation is rotated.

An enzyme electrode operated in this mode has an increased response. At the time interval when the electrode is disconnected the product of the enzymatic reaction is accumulated near the electrode, a larger amount of the product of the enzymatic reaction reacts at the electrode compared with such electrode connected continuously, and the current is higher.

A higher sensitivity is obtained by the integration of the current signal. The integration is effected digitally by the computer which considerably increases the signal to noise ratio. Such integration starts a few milliseconds after application of the potential on the electrode at each cycle and thus interference from double layer charging and other surface reactions are suppressed.

The system of the invention can be used for quantitative measurements of a high degree of sensitivity, with sensitivities in the picogram/ml range. The system can also be used for screening procedures (such as for example for the presence or absence of breast cancer and other malignancies).

The assays can be based on a variety of enzymes, one of the enzymes of choice being alkaline phosphatase. Other enzymes which can be used are of the hydrolase type, such as aryl galactosidase; dehydrogenases such as alcohol dehydrogenase, glucose dehydrogenase, etc.; oxidases such as glucose oxidase, alcohol oxidase, etc. The systems can be based on antigen-antibody interaction as well as systems such as hormone-receptor; nucleoside in one strand of a DNA or RNA and the nucleotides in a complementary strand, etc.

In general terms, the analytical system of the invention can be used with systems in which one type of molecule (A) binds specifically with a high binding constant with a second type (B), said binding molecules (A) being capable of being immobilized on a solid inert electrically conductive surface such as glassy carbon, graphite, gold, etc., such bound (A) molecules being able to interact and bind to said (B) type molecules which will be specifically adsorbed on the electrode surface.

According to one embodiment of the invention, the electrochemical assay can be carried out with alkaline phosphatase. This is effected with such alkaline phosphatase attached to an electrode, where the substrate is p-aminophenyl phosphate. This substrate was prepared for this purpose from nitrophenyl phosphate, by catalytic hydrogen reduction of the nitro group in the presence of platinum oxide. The thus obtained aminophenyl phosphate is perfect for use with the above described sensor. The assay is effected as set out above, and the product of the enzymatic hydrolysis is amino-phenol which is easily oxidized at a carbon electrode: the electrochemical determination of alkaline phosphatase using this substrate occurs at a low overvoltage of the order of about 0.2 V versus SCE, and the electrode reaction is free of phenomena such as adsorption or fouling. The invention is illustrated in the following with reference to antigens and antibodies. It can be used for the quantitative assay of corresponding systems such as hormones, receptors, nucleotides of complementary nucleic acids and the like. The assay can be based on competition reactions, on sandwich type reactions, etc.

Representative stages of an assay according to the invention are:

A. Equal quantities of antibodies are immobilized on each one of the electrodes (by covalent binding or simply by adsorption).

B. In a competition assay, each electrode is allowed to react with a solution in a test tube which contains the antigen, the concentration of which is to be measured, together with a known amount of the antigen conjugated to an enzyme.

In the sandwich-type assay, each electrode is allowed to react with a solution containing the antigen, the concentration of which is to be measured.

C. All the electrodes are washed in a solution containing a detergent and in some cases also bovine serum albumin.

In the competition procedure the assay is continued from stage E, and stage D is skipped.

D. In the sandwich procedure the electrodes are inserted into a beaker containing a solution of a second antibody conjugated to an enzyme (e.g. alkaline phosphatase) and allowed to interact with this solution. The electrodes are then washed with a detergent solution.

E. The whole electrode assembly is inserted in an electrochemical cell containing a buffer solution which is optimal for the enzyme action and the electrodes are connected to a potentiostat which is connected to the microcomputer. Each electrode is also connected to an electronic switch which is connected to a parallel port of the computer.

The chrono-coulometric mode is then applied for the detection of the enzyme amount on each one of the electrodes. In the beginning of the electrochemical measurement all the electrodes are operated together, connected and disconnected repeatedly, which shortens the time of their equilibration. After this the computer scans all the electrodes via the parallel port, and the background response to the potential application of each electrode is recorded by the computer. The substrate for the enzyme is then added to the cell and the response of each electrode is recorded and integrated by the computer. The whole electrochemical measurement sequence can be completed in about two minutes after the addition of the substrate. The response of each electrode is related to the amount of enzyme on that electrode.

The electrochemical measurements do not affect the immunological interactions, and thus it is possible to continue the last incubation stage after the electrochemical stage.

The electrodes can be washed and then used to react with the solutions containing the alkaline phosphatase conjugates for a longer period of time and then the electrochemical assay can be repeated. This is impossible with immunoassays using the ELISA technique.

F. In cases where the electrodes surfaces are not identical, the system can be calibrated by measuring the oxidation or reduction of an electroactive species such as oxidation of ferrocyanide in the electrochemical cell and comparison of the results of all the electrodes.

An enzyme of choice for use in the assay of the invention, is alkaline phosphatase attached to an electrode in which the substrate is p-aminophenyl phosphate. This substrate was synthesized from nitrophenyl phosphate. The synthesis was carried out by catalytic hydrogen reduction of the nitro group in the presence of platinum oxide (1). The product of the enzymatic hydrolysis is amino phenol which is easily oxidized at an inert electrode such as a carbon electrode. Thus the electrochemical determination of alkaline phosphatase using this substrate occurs at low over voltage (~0.2 volts vs SCE) and the electrode reaction is free of problems such as adsorption and fouling. The following examples are to be construed in a non-limitative manner.

EXAMPLES

A. Anti-mouse IgG (200 nanogram) were covalently bound by the carbodiimide method (3) to carbon electrodes of 0.07 cm$^2$ area (glassy carbon or graphite). The electrodes were then allowed to react with 0.25 ml of mouse IgG (24 microgram/ml) for 1 hour and then with a second antibody directed against mouse IgG and conjugated to alkaline phosphatase (Bio-Yeda catalog No. 3465-1) diluted 1:500 again for 1 hour. The amount of IgG in the test samples could be calculated from the electrode response.

B. Antibodies against aldosterone were bound to the electrodes and the electrodes were allowed to react for 30 minutes with test samples containing unknown amounts of aldosterone and known amount of aldosterone conjugated to alkaline phosphatase. The aldosterone concentration in the test sample can be measured with a sensitivity in the picogram/ml range.

MULTIELECTRODE SYSTEM

Clinical tests in hospital and clinical laboratories usually involve a large number of samples. In addition, measurements based on biologically active materials such as enzymes and antibodies do need calibration curves and standards. Hence a system capable of simultaneous measurements will be preferred.

A multielectrode system which allows the simultaneous determination of different samples has been designed. An instrument composed of eight electrodes has been built and successfully tested.

The instrument is composed of an ensemble of identical electrodes made of glassy carbon in a rod shape embedded in teflon. The electrodes assembly is connected to the potentiostat and is also connected via a multiplexer to a parallel port of the microcomputer. The electrodes are all inserted in an electrochemical cell containing a reference electrode and a counter electrode which are also connected to the potentiostat. Each electrode can be electrically disconnected for some time interval and then connected again in a repeated mode. An enzyme electrode operating in this mode has increased response. At the time interval when the electrode is disconnected the product of the enzymatic reaction is accumulated near the electrode. Thus, when a potential is applied for a short time interval on the electrode, a larger amount of the product of the enzymatic reaction reacts at the electrode than if the electrode is connected continuously and the current is higher. In addition, higher sensitivity is obtained by integration of the current signal. The integration which is done digitally by the computer considerably increases the signal to noise ratio. The integration starts few milliseconds after application of the potential on the electrode at each cycle and thus interference from double layer charging and other surface reactions is supressed. The time when the electrode is disconnected is used for the detection of other electrodes. Thus, with a computer controlled electronic switching one can measure many electrodes in the same solution. Since the enzyme is confined only to the electrode surface there are no interferences between the electrodes.

The instrument built enables the simultaneous determination of samples on eight electrodes. Similar devices containing a larger number of electrodes can be prepared. It considerably reduces the time needed for the electrochemical assay. In addition, since all the electrodes are tested in the same solution and their response to the addition of the same amount of substrate is checked, errors introduced by dilutions etc. are minimized.

This multielectrode system was tested using the mode system mouse immunoglobulins and also the hormone $\beta$HCG.

DISPOSABLE ELECTRODES

Rather then devise a reusable electrode in which a recovery procedure is required, we, recently, worked out a procedure employing very inexpensive disposable electrode systems.

Three types of carbon electrodes were tested: carbon paper, carbon cloth and carbon felts. Among the three, the carbon felt electrodes have the highest reproducibility. The carbon felt was cut into small discs (diameter—4 mm and height—0.6 mm).

The immunoassays were carried out using the model system mouse IgG Antimouse IgG (polyclonal) were covalently coupled to carbon felt discs by the use of EDC. The discs were left overnight in a solution containing the antibodies and EDC (10:1 w/w). The discs were then washed and allowed to react with a solution containing mouse IgG (diluted 1:1000) for 1 hour, and then with a solution of antimouse IgG conjugated to alkaline phosphatase again for 1 hour. At this stage each disc was mounted on a teflon rod to which a platinum wire was inserted for electrical connection. The discs were then checked electrochemically for alkaline phosphatase activity using the same assay described for the glassy carbon electrodes. Table III summarizes the results obtained with the carbon felt electrodes and mouse IgG system.

DETERMINATION OF THE HORMONE $\beta$HCG.

Two procedures have been developed and tested for the hormone $\beta$HCG.

A. The sandwich procdure: Ponyclonal antibodies against HCG (aHCG) were covalently bound to glassy carbon electrodes. The electrodes were then allowed to react with test samples containing unknown amount of the hormone for 1 hour, and then washed and transferred to a solution containing monoclonal antibodies against HCG conjugated to alkaline phosphatase (ap-a $\beta$HCG)and incubated for 1 hour. From the electrochemical assay which followed, the hormone concentration could be determined.

B. The double sandwich procedure: Monoclonal antibodies against $\beta$HCG were attached to glassy carbon electrodes by covalent binding or even by simple adsorption. The electrodes were then allowed to react with test samples containing unknown amount of the hormone for 1 hour at 37° C. and then washed and transferred to a beaker containing polyclonal antibodies against HCG which were produced in a rabbit, and incubated at 37° for 1 hour. The electrodes were then transferred to a solution containing antibody against rabbit immunoglobulins conjugated to alkaline phosphatase, (ap-arb IgG) and then washed and tested electrochemically for alkaline phosphatase activity. From the electrochemical assay the hormone concentration could be determined. FIG. 4 shows results obtained by the determination of $\beta$HCG in urine samples. From FIG. 9 it is obvious that the double sandwich procedure described in procedure B is more sensitive. It involves an additional incubation step compare to procedure A, but on the other hand the alkaline phosphatase conjugates used are less expensive and are commercially available. Hence, at the next stages we focused our attention in standardization and optimization of the the βHCG assay according to procedure B.

The following results were obtained using monoclonal and polyclonal antibodies against HCG purchased from Bio-Makor, Israel, and antirabbit conjugates purchased from Sima, U.S.A. Table I summarizes a a set of experiments in which the hormone was measured in PBS solutions.

TABLE I

| | Determination of βHCG in buffer solutions | | | | | | |
|---|---|---|---|---|---|---|---|
| βHCG U/L | 0 | 10 | 20 | 40 | 80 | 160 | 320 |
| Q uC | 2.03 | 2.75 | 2.45 | 4.86 | 7.91 | 8.57 | 17.0 |
| n | 12 | 17 | 8 | 20 | 16 | 13 | 1 |
| SD | 0.41 | 0.65 | 1.27 | 2.72 | 5.54 | 4.3 | — |

βHCG U/L = the concentration of HCG [units/Liter]
Q = Average electrode response in microcoulomb/10 seconds
n = no of electrodes tested at each concentration
SD = standard deviation at each concentration In another set of experiments serum samples containing a known amount of βHCG (determined by the radioimmunoassay) were diluted in PBS and measured for the hormone (FIG. 5)

Table II summarizes a set of experiments in which the hormone HCG was added to serum samples diluted 1:5 in PBS. These serum samples were tested for the hormone by the radio immunoassay technique and were found negative.

TABLE II

| | Determination of βHCG added to serums | | | |
|---|---|---|---|---|
| βHCG U/L | 0 | 40 | 80 | 160 |
| Q uC | 1.57 | 3.00 | 4.62 | 5.47 |
| n | 3 | 2 | 10 | 3 |
| SD | 0.21 | 0.60 | 1.77 | 1.27 |

In parallel to the elelctrochemical determination we routinely measured the reagents used by application the standart ELISA technique. In general, the results obtained by the ELISA technique showed a high background and the lowest detection limit was much higher compared with those obtained by the electrochemical measurement.

TABLE III

Mouse IgG measured by carbon felt discs
(Each electrode checked separately)
Measurements were carried out in duplicates (I and II)

| amIgG ug/ml | IgG ug/ml | amIgG (dilution) | Q I (uC) | Q II (uC) | Ave u(uC) |
|---|---|---|---|---|---|
| 0.5 | 10 | 1:500 | 47.5 | 40 | 43.7 |
| " | " | 1:1000] | 43 | 30 | 36.5 |
| " | — | 1:500 | 10.9 | 13 | 11.9 |
| " | — | 1:1000 | 4 | 4.2 | 4.1 |
| 20 | 10 | 1:500 | 157 | 109 | 133 |
| " | " | 1:1000 | 63.6 | 60 | 61.8 |
| " | — | 1:500 | 19 | 20 | 19.5 |
| " | — | 1:1000 | 7 | 5.2 | 6.1 |

These results demonstrate that the sensitivity attainable with the carbon felts is even higher then that of the glassy carbon.

The carbon felts were also integrated into the multi-electrode system. Results are summarized in Table IV.

TABLE IV

| amIgG ug/ml | IgG ug/ml | amIgG-A (dilution) | Q I (uC) | Q II (uC) | Ave u(uC) |
|---|---|---|---|---|---|
| 0.5 | 10 | 1:500 | 124 | 86 | 105 |
| " | " | 1:1000 | 60 | 85 | 72.5 |
| " | — | 1:500 | 17.8 | 12 | 14.9 |
| " | — | 1:1000 | 10.8 | 10.9 | 10.9 |

Measurements were taken in duplicates (I and II)

Biotin Labeled Antigens

The highly specific and strong binding of biotin to avidin was utilized for the determination of mouse IgG. Biotin can also be attached to sugars, DNA, etc. and hence the method described can be used for the determination of biological interactions in general.

Figure 7:
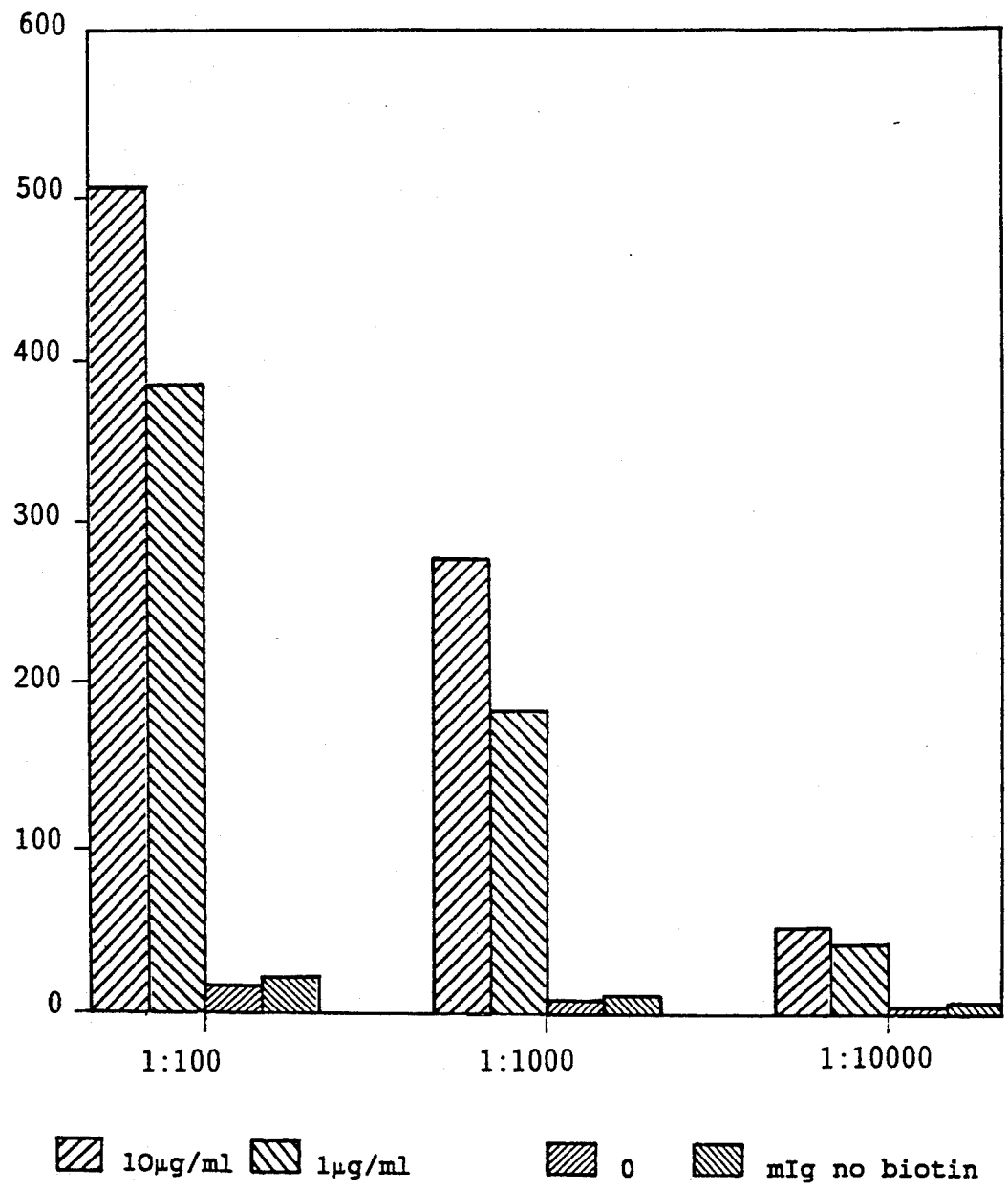
FIG. 7 illustrates the system of MIG-Biotin-Carbon felts.
Figure 8:
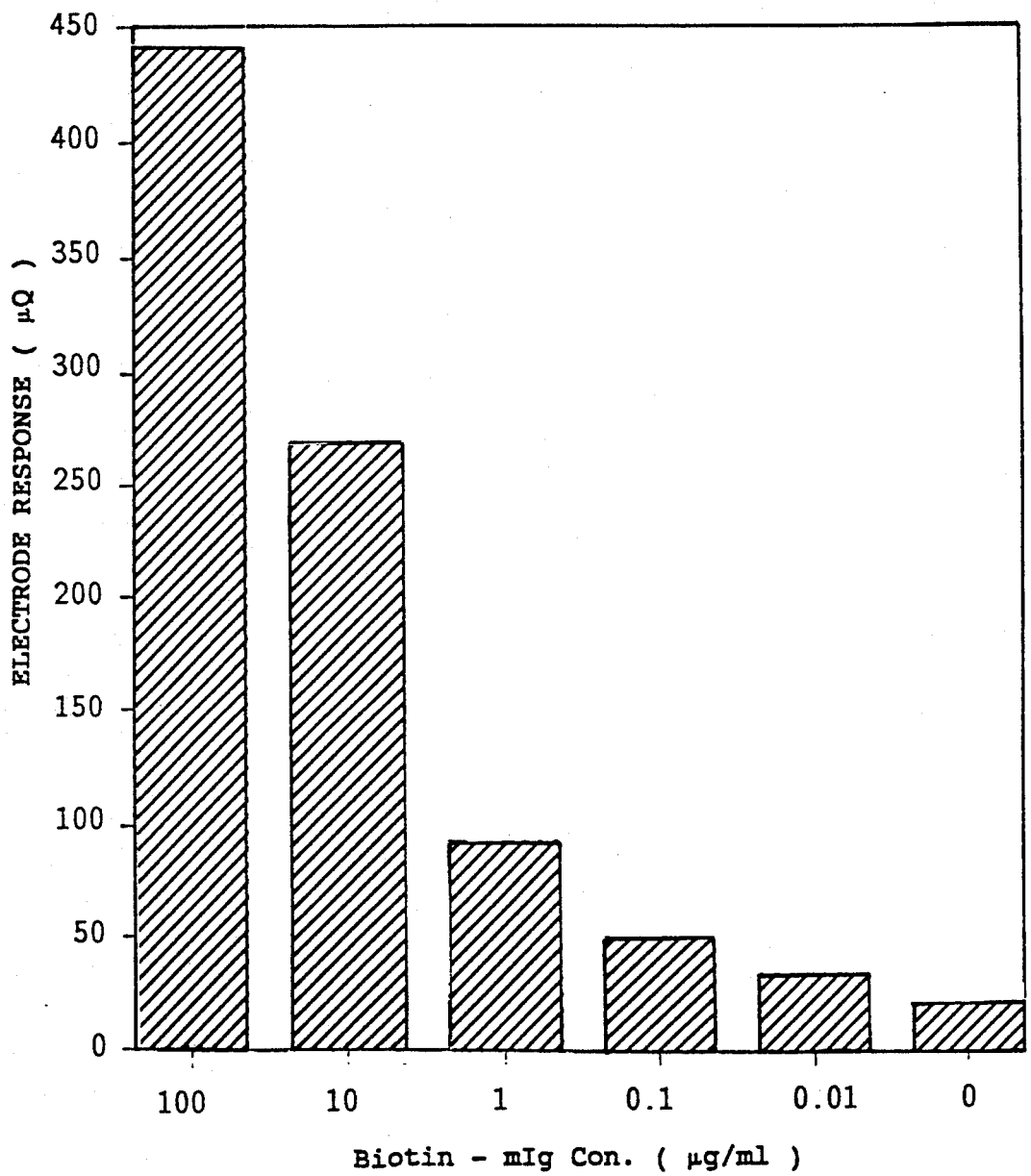
FIG. 8 illustrates the system of Biotin-MIG-carbon felts.

Mouse antibodies were labeled by biotin by the N-hydroxy succinimide method (Bayer E.A. and Wilchek M, 1980, in "Methods of Biochemical Analysis", 26, 1–45). Extra Avidin Alkaline phosphatase conjugates were purchased from Biomakor. Carbon felt Type RVG 1000 purchased from Carbon Lorraine France was used for preparation of the disposable electrodes. The felt was cut into disk 4 mm diameter and 0.6 mm thick. Antimouse IgG were immobilized on the carbon by the carbodiimide method. The carbon felt disks were left overnight in a solution containing 20 microgram/ml antimouse IgG and 2 microgram/ml EDC at room temperature. The disks were then washed in Tris buffer and transferred into Elisa plates (a carbon disk per well) and incubated with mouse IgG solution for one hour at different concentrations. The disks were then washed and incubated with solution containing extra avidin conjugated to alkaline phophatase. After washing the disks were mounted on a teflon holder and attached to platinum wire for electrical; connection and were then tested for alkaline phophatase activity. The alkaline phosphatase activity was related to the mouse IgG concentration. Results are summarized in FIG. 7 and FIG. 8.

F. A droplet (5 microliters) of a solution containing monoclonal antibodies against viral antigen associated with breast cancer were dried on glassy carbon electrodes. The electrode were then allowed to react for 1 hour at 37° with sera (diluted by 10) or plural fluid (diluted up to 500) of patient suffering from breast cancer and patients that do not have the disease. The electrodes were then allowed to react with alkaline phosphatase conjugates to monoclonal antibodies against the viral antigen and for 1 hour at 37° or for 16 hours at room temperature then tested electrochemically. The electrochemical measurement showed the existence of the antigen in the patients suffering from the disease. This provides a sensitive test for determining the presence or absence of breast cancer. Other examples that are currently tested are the detections of other hormones such as T3 and T4 and insulin levels (in blood or urine).

REFERENCES:

1. J. C. Moffart and H. G. Khorana, J. Am.Chem.Soc. 79, 3741, (1957)
2. F. W. Scheller, F. Schubert, R. Renneberg, H. G. Muller, M. Janchen & H. Weise, Biosensors, 1, 135, 1985.
3. Laval, Bourdillon & Moiroux, J. of Amer. Chem. Soc. 106 4701 (1984).

We claim:

1. Apparatus for the sequential rapid qualitative or quantitative assay of a plurality of samples of members of biospecific binding pairs by coulometric measurement, comprising:
   a plurality of working electrodes corresponding to the number of samples to be assayed, said electrodes immersed in a common solution in a vessel,
   a multiplexer for effecting sequential coulometric measurements,
   a potentiostat;
   there being provided in said vessel a reference electrode and a counter electrode, means for applying a predetermined voltage during each such measurement;
   which measurements are that of the electric charge passing between each working electrode and the evaluation thereof indicating the quantity of one of the members of the biospecific binding pairs, or its presence, said working electrodes comprising an electrically inert support which supports a member selected from the group consisting of carbon felt, carbon paper or carbon cloth to which there is firmly bonded one of the biospecific pair members which specifically binds the second complementary member, which second member is tagged by an enzyme or which second member is coupled to at least one further biospecific member, the last of which further biospecific members is tagged with an enzyme;
   whereby when the electrodes are introduced into a substrate of the enzyme, a coulometric signal is formed, thereby sequentially measuring said samples.

2. Apparatus according to claim 1 wherein each working electrode comprises a carbon felt attached to an electrically non-conducting inert support, said felt being electrically connected to the multiplexer.

3. Apparatus according to claim 1 wherein one of the members of the biospecific binding pairs is bonded to the carbon felt, paper or cloth of the working electrode by a carbodiimide linkage.

4. An apparatus according to claim 1 further comprising means for rotating the working electrodes during the incubation of the two members of the binding pair or during the time of measurement.

5. An apparatus according to claim 1 wherein means are provided for connecting and disconnecting at will the potential applied to the working electrodes between measurements.

6. An assay for the qualitative or quantitative sequential determination of a plurality of samples of members of specific binding pairs selected from the group consisting of antibodies/antigens, hormones, receptors, and nucleotides/nucleotide probes, wherein a first member of a pair is immobilized in an apparatus as claimed in claim 1, wherein the method comprises:
   (a) contacting the working electrode with a sample containing the second member of the pair, said second member being labelled with an enzyme, so as to bind said second member to the first member immobilized on the electrode,
   (b) immersing the electrode into a solution containing a substrate of the enzyme,
   (c) generating a coulometric signal,
   (d) measuring and evaluating said signal, and
   (e) repeating said assay sequentially for each sample.

7. A sequential assay according to claim 6 wherein a known amount of biotin-tagged antigen is present together with an unknown amount of the same antigen in an aqueous system, wherein an antibody is bound to the working electrode, and where the antibody bound to the electrode reacts with a biotin-labelled antigen and an unlabeled antigen followed by incubation with an avidin-conjugated enzyme, wherein one of the members of the biotin-tagged antigen and the avidin-conjugated enzyme is bonded to a carbon felt, carbon paper or carbon cloth by a carbodiimide linkage.

8. An assay according to claim 6 wherein the linkage of the one member of the biospecific binding pair to the carbon felt of the working electrode is via a linkage selected from the group consisting of carbodiimide or biotin-avidin linkage.

9. An assay according to claim 6 wherein the working electrodes are rotated during the period of incubation of the binding pair and during the time of the actual coulometric measurement.

10. An assay according to claim 6 wherein the working electrodes are rotated during the period of incubation and during the period of time of actual coulometric measurement.

11. An assay according to claim 6 wherein means are provided for disconnecting any of the working electrodes during the period between actual measurement, and reconnecting said electrodes to the source of electric potential during the measurement.

* * * * *